(12) United States Patent
Shalev

(10) Patent No.: US 8,486,131 B2
(45) Date of Patent: Jul. 16, 2013

(54) EXTRA-VASCULAR WRAPPING FOR TREATING ANEURYSMATIC AORTA IN CONJUNCTION WITH ENDOVASCULAR STENT-GRAFT AND METHODS THEREOF

(75) Inventor: Alon Shalev, Ra'anana (IL)

(73) Assignee: Endospan Ltd., Netanya (IL)

( * ) Notice: Subject to any disclaimer, the term of this patent is extended or adjusted under 35 U.S.C. 154(b) by 194 days.

(21) Appl. No.: 12/808,037

(22) PCT Filed: Dec. 15, 2008

(86) PCT No.: PCT/IL2008/001621
§ 371 (c)(1),
(2), (4) Date: Jun. 14, 2010

(87) PCT Pub. No.: WO2009/078010
PCT Pub. Date: Jun. 25, 2009

(65) Prior Publication Data
US 2010/0292774 A1   Nov. 18, 2010

Related U.S. Application Data

(60) Provisional application No. 61/014,031, filed on Dec. 15, 2007.

(51) Int. Cl.
*A61F 2/958* (2013.01)
(52) U.S. Cl.
USPC .................................................. 623/1.11
(58) Field of Classification Search
USPC ............... 623/1.11, 1.13–1.16, 1.21, 1.22, 623/1.27, 1.25, 1.3, 1.34–1.36, 1.42–1.44, 623/1.46; 606/194, 198, 108, 153, 191, 195, 606/151, 155, 158
See application file for complete search history.

(56) References Cited

U.S. PATENT DOCUMENTS

| 4,355,426 A | 10/1982 | MacGregor |
| 4,505,767 A | 3/1985 | Quin |

(Continued)

FOREIGN PATENT DOCUMENTS

| CA | 2 497 704 | 3/2004 |
| EP | 1 177 780 | 2/2002 |

(Continued)

OTHER PUBLICATIONS

"E-vita® open plus" product brochure (JOTEC GmbH, Hechingen, Germany), 2010.

(Continued)

*Primary Examiner* — Kathleen Holwerda
*Assistant Examiner* — Jocelin Tanner
(74) *Attorney, Agent, or Firm* — Sughrue Mion, PLLC

(57) ABSTRACT

A system for treating an aneurysmatic abdominal aorta, comprising (a) an extra-vascular wrapping (EVW) comprising (i) at least one medical textile member adapted to at least partially encircle a segment of aorta in proximity to the renal arteries, and (ii) a structural member, wherein EVW is adapted for laparoscopic delivery, and (b) an endovascular stent-graft (ESG) comprising (i) a compressible structural member, and (ii) a substantially fluid impervious fluid flow guide (FFG) attached thereto. Also described is an extra-vascular ring (EVR) adapted to encircle the neck of an aortic aneurysm. Further described are methods for treating an abdominal aortic aneurysm, comprising laparoscopically delivering the extra-vascular wrapping (EVW) and endovascularly placing an endovascular stent-graft (ESG). Also described are methods to treat a type I endoleak.

14 Claims, 11 Drawing Sheets

U.S. PATENT DOCUMENTS

| | | |
|---|---|---|
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,122,136 A | 6/1992 | Guglielmi et al. |
| 5,133,732 A | 7/1992 | Wiktor |
| 5,234,448 A * | 8/1993 | Wholey et al. ................ 606/153 |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,554,181 A | 9/1996 | Das |
| 5,562,724 A | 10/1996 | Vorwerk et al. |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,777 A | 5/1998 | Chuter |
| 5,769,882 A | 6/1998 | Fogarty et al. |
| 5,769,884 A * | 6/1998 | Solovay ........................ 623/1.13 |
| 5,782,903 A | 7/1998 | Wiktor |
| 5,782,906 A | 7/1998 | Marshall et al. |
| 5,824,040 A | 10/1998 | Cox et al. |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 6,015,431 A | 1/2000 | Thornton et al. |
| 6,033,435 A | 3/2000 | Penn et al. |
| 6,049,824 A | 4/2000 | Simonin |
| 6,099,497 A | 8/2000 | Adams et al. |
| 6,117,145 A | 9/2000 | Wood et al. |
| 6,156,064 A * | 12/2000 | Chouinard ................... 623/1.44 |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,290,720 B1 | 9/2001 | Khosravi et al. |
| 6,296,661 B1 | 10/2001 | Davila et al. |
| 6,325,823 B1 | 12/2001 | Horzewski et al. |
| 6,344,056 B1 * | 2/2002 | Dehdashtian ................ 623/1.35 |
| 6,406,420 B1 * | 6/2002 | McCarthy et al. .............. 600/16 |
| 6,428,565 B1 | 8/2002 | Wisselink |
| 6,506,211 B1 | 1/2003 | Skubitz et al. |
| 6,613,078 B1 | 9/2003 | Barone |
| 6,635,083 B1 | 10/2003 | Cheng et al. |
| 6,648,911 B1 * | 11/2003 | Sirhan et al. ................. 623/1.15 |
| 6,652,567 B1 | 11/2003 | Deaton |
| 6,656,214 B1 | 12/2003 | Fogarty et al. |
| 6,692,520 B1 | 2/2004 | Gambale et al. |
| 6,695,833 B1 | 2/2004 | Frantzen |
| 6,743,195 B2 | 6/2004 | Zucker |
| 6,752,826 B2 * | 6/2004 | Holloway et al. ............ 623/1.13 |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,964,679 B1 | 11/2005 | Marcade et al. |
| 6,986,774 B2 | 1/2006 | Middleman et al. |
| 7,008,441 B2 | 3/2006 | Zucker |
| 7,044,962 B2 | 5/2006 | Elliott |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,144,421 B2 | 12/2006 | Carpenter et al. |
| 7,201,772 B2 | 4/2007 | Schwammenthal et al. |
| 7,223,266 B2 | 5/2007 | Lindenbaum et al. |
| 7,270,675 B2 | 9/2007 | Chun et al. |
| 7,279,003 B2 | 10/2007 | Berra et al. |
| 7,294,147 B2 | 11/2007 | Hartley |
| 7,306,623 B2 | 12/2007 | Watson |
| 7,341,598 B2 | 3/2008 | Davidson et al. |
| 7,407,509 B2 | 8/2008 | Greenberg et al. |
| 7,429,269 B2 | 9/2008 | Schwammenthal et al. |
| 7,442,204 B2 | 10/2008 | Schwammenthal et al. |
| 7,473,272 B2 | 1/2009 | Pryor |
| 7,537,609 B2 | 5/2009 | Davidson et al. |
| 7,540,881 B2 | 6/2009 | Meyer et al. |
| 7,544,160 B2 | 6/2009 | Gross |
| 7,637,939 B2 | 12/2009 | Tischler |
| 7,662,161 B2 | 2/2010 | Briganti et al. |
| 7,662,168 B2 | 2/2010 | McGuckin, Jr. et al. |
| 7,678,141 B2 | 3/2010 | Greenan et al. |
| 7,722,626 B2 | 5/2010 | Middleman et al. |
| 7,731,732 B2 | 6/2010 | Ken |
| 7,815,673 B2 | 10/2010 | Bloom et al. |
| 7,959,662 B2 | 6/2011 | Erbel et al. |
| 8,021,418 B2 | 9/2011 | Gerberding et al. |
| 2001/0014823 A1 | 8/2001 | Ressemann et al. |
| 2001/0044652 A1 | 11/2001 | Moore |
| 2001/0053930 A1 | 12/2001 | Kugler et al. |
| 2002/0040236 A1 | 4/2002 | Lau et al. |
| 2002/0099438 A1 | 7/2002 | Fursty |
| 2002/0099441 A1 | 7/2002 | Dehdashtian |
| 2002/0123791 A1 | 9/2002 | Harrison |
| 2002/0156495 A1 | 10/2002 | Brenneman et al. |
| 2003/0093145 A1 | 5/2003 | Lawrence-Brown et al. |
| 2003/0125796 A1 | 7/2003 | Dong |
| 2003/0130720 A1 | 7/2003 | DePalma et al. |
| 2003/0144725 A1 | 7/2003 | Lombardu |
| 2003/0153968 A1 | 8/2003 | Geis et al. |
| 2003/0199967 A1 | 10/2003 | Hartley et al. |
| 2003/0199968 A1 | 10/2003 | Ainsworth et al. |
| 2003/0212449 A1 | 11/2003 | Cox |
| 2003/0236567 A1 | 12/2003 | Elliot |
| 2004/0015227 A1 | 1/2004 | Vardi et al. |
| 2004/0106972 A1 | 6/2004 | Deaton |
| 2004/0106978 A1 | 6/2004 | Greenberg et al. |
| 2004/0133266 A1 * | 7/2004 | Clerc et al. ................... 623/1.22 |
| 2004/0171978 A1 | 9/2004 | Shalaby |
| 2004/0181149 A1 | 9/2004 | Langlotz et al. |
| 2004/0215327 A1 | 10/2004 | Doig et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0149166 A1 | 7/2005 | Schaeffer et al. |
| 2005/0171598 A1 | 8/2005 | Schaeffer et al. |
| 2005/0203606 A1 | 9/2005 | VanCamp |
| 2005/0222668 A1 | 10/2005 | Schaeffer et al. |
| 2005/0222669 A1 | 10/2005 | Purdy |
| 2005/0266042 A1 * | 12/2005 | Tseng ........................... 424/423 |
| 2005/0283188 A1 | 12/2005 | Loshakove et al. |
| 2006/0015170 A1 | 1/2006 | Jones et al. |
| 2006/0052799 A1 | 3/2006 | Middleman et al. |
| 2006/0069426 A1 | 3/2006 | Weinberger |
| 2006/0100684 A1 | 5/2006 | Elliott |
| 2006/0149360 A1 | 7/2006 | Schwammenthal et al. |
| 2006/0155358 A1 | 7/2006 | LaDuca et al. |
| 2006/0155366 A1 | 7/2006 | LaDuca et al. |
| 2006/0167476 A1 | 7/2006 | Burdulis, Jr. et al. |

| | | | | | | |
|---|---|---|---|---|---|---|
| 2006/0193892 | A1 | 8/2006 | Furst et al. | WO | 2006/007389 | 1/2006 |
| 2006/0229709 | A1 | 10/2006 | Morris et al. | WO | 2006/028925 | 3/2006 |
| 2006/0241740 | A1 | 10/2006 | Vardi et al. | WO | 2006/070372 | 7/2006 |
| 2006/0271166 | A1 | 11/2006 | Thill et al. | WO | 2007/084547 | 7/2007 |
| 2006/0281966 | A1* | 12/2006 | Peacock, III ............... 600/37 | WO | 2007/144782 | 12/2007 |
| 2007/0021822 | A1 | 1/2007 | Boatman | WO | 2008/008291 | 1/2008 |
| 2007/0043425 | A1 | 2/2007 | Hartley et al. | WO | 2008/035337 | 3/2008 |
| 2007/0055350 | A1 | 3/2007 | Erickson et al. | WO | 2008/042266 | 4/2008 |
| 2007/0055358 | A1 | 3/2007 | Krolik et al. | WO | 2008/047092 | 4/2008 |
| 2007/0060989 | A1 | 3/2007 | Deem et al. | WO | 2008/047354 | 4/2008 |
| 2007/0073373 | A1 | 3/2007 | Bonsignore | WO | 2008/053469 | 5/2008 |
| 2007/0088425 | A1 | 4/2007 | Schaeffer | WO | 2008/107885 | 9/2008 |
| 2007/0112344 | A1 | 5/2007 | Keilman | WO | 2008/140796 | 11/2008 |
| 2007/0135677 | A1 | 6/2007 | Miller et al. | WO | 2009/078010 | 6/2009 |
| 2007/0142896 | A1 | 6/2007 | Anderson et al. | WO | 2009/116041 | 9/2009 |
| 2007/0150051 | A1 | 6/2007 | Arnault de la Menardiere et al. | WO | 2009/116042 | 9/2009 |
| 2007/0156167 | A1 | 7/2007 | Connors et al. | WO | 2009/118733 | 10/2009 |
| 2007/0167898 | A1 | 7/2007 | Peters et al. | WO | 2010/024869 | 3/2010 |
| 2007/0179598 | A1* | 8/2007 | Duerig ............... 623/1.44 | WO | 2010/024879 | 3/2010 |
| 2007/0185565 | A1 | 8/2007 | Schwammenthal et al. | WO | 2010/031060 | 3/2010 |
| 2007/0208410 | A1 | 9/2007 | Berra et al. | WO | 2010/045238 | 4/2010 |
| 2007/0213805 | A1 | 9/2007 | Schaeffer et al. | WO | 2010/062355 | 6/2010 |
| 2007/0219610 | A1 | 9/2007 | Israel | WO | 2010/088776 | 8/2010 |
| 2007/0219627 | A1* | 9/2007 | Chu et al. ............... 623/1.36 | WO | 2010/128162 | 11/2010 |
| 2007/0233229 | A1 | 10/2007 | Berra et al. | WO | 2010/150208 | 12/2010 |
| 2007/0237973 | A1 | 10/2007 | Purdy et al. | WO | 2011/004374 | 1/2011 |
| 2007/0244542 | A1 | 10/2007 | Greenan et al. | WO | 2011/007354 | 1/2011 |
| 2007/0244543 | A1 | 10/2007 | Mitchell | WO | 2011/055364 | 5/2011 |
| 2007/0244547 | A1 | 10/2007 | Greenan | WO | 2011/064782 | 6/2011 |
| 2007/0255388 | A1 | 11/2007 | Rudakov et al. | WO | 2011/067764 | 6/2011 |
| 2008/0002871 | A1 | 1/2008 | Gunzert-Marx et al. | WO | 2011/070576 | 6/2011 |
| 2008/0015673 | A1 | 1/2008 | Chuter | WO | 2011/080738 | 7/2011 |
| 2008/0058918 | A1 | 3/2008 | Watson | WO | 2011/095979 | 8/2011 |
| 2008/0109066 | A1 | 5/2008 | Quinn | WO | 2011/106532 | 9/2011 |
| 2008/0114445 | A1 | 5/2008 | Melsheimer et al. | WO | 2011/106533 | 9/2011 |
| 2008/0147173 | A1 | 6/2008 | McIff et al. | WO | 2011/106544 | 9/2011 |
| 2008/0167704 | A1 | 7/2008 | Wright et al. | | | |
| 2008/0195190 | A1 | 8/2008 | Bland et al. | | | |
| 2008/0269789 | A1 | 10/2008 | Eli | | | |
| 2008/0275540 | A1 | 11/2008 | Wen | | | |
| 2008/0275542 | A1 | 11/2008 | LaDuca et al. | | | |
| 2008/0288044 | A1 | 11/2008 | Osborne | | | |
| 2008/0319528 | A1 | 12/2008 | Yribarren et al. | | | |
| 2009/0012597 | A1 | 1/2009 | Doig et al. | | | |
| 2009/0012602 | A1 | 1/2009 | Quadri | | | |
| 2009/0030502 | A1 | 1/2009 | Sun et al. | | | |
| 2009/0048663 | A1 | 2/2009 | Greenberg | | | |
| 2009/0099648 | A1 | 4/2009 | Yu | | | |
| 2009/0099649 | A1 | 4/2009 | Chobotov et al. | | | |
| 2009/0105809 | A1 | 4/2009 | Lee et al. | | | |
| 2009/0112233 | A1 | 4/2009 | Xiao | | | |
| 2009/0125096 | A1 | 5/2009 | Chu et al. | | | |
| 2009/0138067 | A1 | 5/2009 | Pinchuk et al. | | | |
| 2009/0149877 | A1 | 6/2009 | Hanson et al. | | | |
| 2009/0240316 | A1 | 9/2009 | Bruszewski | | | |
| 2009/0248134 | A1 | 10/2009 | Dierking et al. | | | |
| 2009/0254170 | A1 | 10/2009 | Hartley et al. | | | |
| 2009/0259290 | A1 | 10/2009 | Bruszewski et al. | | | |
| 2009/0287145 | A1 | 11/2009 | Cragg et al. | | | |
| 2010/0063575 | A1 | 3/2010 | Shalev | | | |
| 2010/0070019 | A1 | 3/2010 | Shalev | | | |
| 2010/0161026 | A1 | 6/2010 | Brocker et al. | | | |
| 2010/0292774 | A1 | 11/2010 | Shalev | | | |
| 2011/0093002 | A1 | 4/2011 | Rucker et al. | | | |
| 2011/0208289 | A1 | 8/2011 | Shalev | | | |
| 2011/0208296 | A1 | 8/2011 | Duffy et al. | | | |
| 2011/0208297 | A1 | 8/2011 | Tuval et al. | | | |
| 2011/0208298 | A1 | 8/2011 | Tuval et al. | | | |
| 2011/0218607 | A1 | 9/2011 | Arbefeuille et al. | | | |
| 2011/0264184 | A1 | 10/2011 | Heltai | | | |

FOREIGN PATENT DOCUMENTS

| | | |
|---|---|---|
| EP | 1 325 716 | 7/2003 |
| JP | 2002-253682 | 9/2002 |
| WO | 2004/017868 | 3/2004 |
| WO | 2005/002466 | 1/2005 |
| WO | 2005/037138 | 4/2005 |
| WO | 2005/041781 | 5/2005 |
| WO | 2005/041783 | 5/2005 |

OTHER PUBLICATIONS

Fonseca A et al., "Intravascular ultrasound assessment of the novel AngioSculpt scoring balloon catheter for the treatment of complex coronary lesions," J Invasive Cardiol 20(1):21-7 (Jan. 2008).

Khlif H et al., "Contribution to the Improvement of Textile Vascular Prostheses Crimping," Trends in Applied Sciences Research 6(9):1019-1027 (2011).

An International Search Report dated Sep. 29, 2008, which issued during the prosecution of Applicant's PCT/IL08/000287.

A Written Opinion dated Sep. 29, 2008, which issued during the prosecution of Applicant's PCT/IL08/000287.

An International Search Report dated Feb. 4, 2011, which issued during the prosecution of Applicant's PCT/IB2010/052861.

A Written Opinion dated Feb. 4, 2011, which issued during the prosecution of Applicant's PCT/IB2010/052861.

An International Search Report dated Dec. 3, 2010, which issued during the prosecution of Applicant's PCT/IL2010/000564.

A Written Opinion dated Dec. 3, 2010, which issued during the prosecution of Applicant's PCT/IL2010/000564.

An International Search Report dated Nov. 5, 2010, which issued during the prosecution of Applicant's PCT/IL2010/000549.

A Written Opinion dated Nov. 5, 2010, which issued during the prosecution of Applicant's PCT/IL2010/000549.

An International Search Report dated Aug. 4, 2011, which issued during the prosecution of Applicant s PCT/IL2010/000999.

An International Search Report dated Mar. 10, 2011, which issued during the prosecution of Applicant's PCT/IL2010/000917.

An International Search Report dated Mar. 30, 2011, which issued during the prosecution of Applicant's PCT/IL2010/001018.

An International Search Report dated Apr. 18, 2011, which issued during the prosecution of Applicant's PCT/IL2010/001037.

An International Search Report dated May 23, 2011, which issued during the prosecution of Applicant's PCT/IL2010/001087.

An International Search Report dated Jun. 28, 2011, which issued during the prosecution of Applicant's PCT/IL2011/000135.

An International Search Report dated Jun. 30, 2009, which issued during the prosecution of Applicant's PCT/IL2008/001621.

A Written Opinion dated Jun. 30, 2009, which issued during the prosecution of Applicant's PCT/IL2008/001621.

An International Search Report dated Mar. 11, 2009, which issued during the prosecution of Applicant's PCT/IL2007/001312.

A Written Opinion dated Mar. 11, 2009, which issued during the prosecution of Applicant's PCT/IL2007/001312.

An English translation of an Office Action dated Aug. 25, 2011, which issued during the prosecution of Chinese Patent Application No. 200880014919.9.

An Office Action dated Nov. 12, 2010, which issued during the prosecution of U.S. Appl. No. 12/447,684.

An Office Action dated Apr. 27, 2011, which issued during the prosecution of U.S. Appl. No. 12/447,684.

An International Search Report and a Written Opinion both dated Jul. 13, 2012, which issued during the prosecution of Applicant's PCT/IL2012/000083.

An International Search Report and a Written Opinion both dated Mar. 15, 2013, which issued during the prosecution of Applicant's PCT/IL2012/050424.

* cited by examiner

Dress hooks & eyes

Skirt hooks & eyes

Heavy duty hooks & eyes

Coat hooks & eyes

EXTRA-VASCULAR WRAPPING FOR TREATING ANEURYSMATIC AORTA IN CONJUNCTION WITH ENDOVASCULAR STENT-GRAFT AND METHODS THEREOF

FIELD OF THE INVENTION

The present invention generally pertains to an extra-vascular wrapping in the vicinity of the aneurysm neck and specifically the renal arteries for allowing the performance of endovascular aneurysm repair—EVAR—on patients either with aneurysms close to the renal arteries or with type I endoleaks, and methods thereof.

BACKGROUND OF THE INVENTION

U.S. patent application 61/014,031 to the inventor is incorporated hereby by reference in its entirety.

An aneurysm is a localized, blood-filled dilation (bulge) of a blood vessel caused by disease or weakening of the vessel wall. Left untreated, the aneurysm will frequently rupture, resulting in loss of blood through the rupture and death.

Aneurysms may involve arteries or veins and have various causes. They are commonly further classified by shape, structure and location. Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm because no statistically demonstrated benefit exists in performing such procedures.

Aneurysms in the abdominal aorta are associated with a particularly high mortality rate; accordingly, current medical standards call for urgent operative repair when aneurysm diameter is larger than 5 cm. Abdominal surgery, however, results in substantial stress to the body. Although the mortality rate for an aortic aneurysm is extremely high, there is also considerable mortality and morbidity associated with open surgical intervention to repair an aortic aneurysm. Repair of an aortic aneurysm by surgical means is a major operative procedure. Substantial morbidity accompanies the procedure, resulting in a protracted recovery period. Further, the procedure entails a substantial risk of morbidity and mortality, mostly due to the cardiopulmonary bypass employed in such a procedure.

Therefore, less invasive methods have been introduced to attempt to treat an aortic aneurysm without the attendant risks of intra-abdominal surgery. Among them are inventions such as U.S. Pat. No. 4,562,596 which discloses an aortic graft constructed for intraluminal insertion; U.S. Pat. No. 4,787,899 teaches an intraluminal grafting system includes a hollow graft which has a plurality of staples adapted proximate its proximal end. The system includes a guide for positioning the proximal end of the graft upstream in a lumen which may be a blood vessel or artery; and U.S. Pat. No. 5,042,707 which presents a stapler, adapted to be inserted into a blood vessel and moved to a desired position therealong, and having a selectively-articulatable distal marginal end portion used to staple a graft to the interior wall of the blood vessel.

Hence, although in recent years certain techniques have been developed that may reduce the stress, morbidity, and risk of mortality associated with surgical intervention to repair aortic aneurysms, none of the systems that have been developed effectively treat the aneurysm and exclude the affected section of aorta from the pressures and stresses associated with circulation. None of the devices disclosed in the references provide a reliable and quick means to reinforce an aneurysmal artery. In addition, all of the prior references require a sufficiently large section of healthy aorta surrounding the aneurysm to ensure attachment of the graft. The neck of the aorta at the cephalad end (i.e., above the aneurysm) is usually sufficient to maintain a graft's attachment means. However, when an aneurysm is located near the iliac arteries, there may be an ill-defined neck or no neck below the aneurysm. Such an ill-defined neck would have an insufficient amount of healthy aortic tissue to which to successfully mount a graft. Furthermore, much of the abdominal aorta wall may be calcified which may make it extremely difficult to attach the graft to the wall.

Shortcomings of the presently available endovascular stent-graft products include endoleaks, anatomic variability, anatomic non-conformity, migration/dislocation, discontinuities of endoluminal profile and thrombogenicity.

Endoleaks are caused by passage of blood into the aneurismal space subsequent to stent-graft placement. Research has exposed yet another problem which indicates that the necks of the post-surgical aorta increase in size for approximately twelve months, regardless of whether the aneurysm experiences dimensional change. This phenomenon can result in perigraft leaks and graft migration. Anatomic variability: although sizing of "tube" or "bifurcated" grafts is radiographically assessed prior to surgery, it is necessary for the surgeon to have a large selection of graft lengths and diameters on hand to ensure an appropriate surgical outcome. Anatomic non-conformity: placement of a circularly-profiled graft with an associated fixation device within an essentially "ovoid"-profiled vessel. Migration/dislocation also caused due to the use of attachment means which fasten only to the insubstantial, structurally compromised (diseased) intima and media levels of the vessel wall. Discontinuities of endoluminal profile are potential contributors to hemodynamic disturbances that might lead to non laminar, or even turbulent flow regimen. This in turn can contribute to increased clot formation. Thrombogenicity: manufactured of synthetic polymers, contemporary vascular liners present a luminal surface that is typically far more thrombogenic than the native arterial intimal tissue such devices cover.

Unfavorable anatomy relating to the neck of the aneurysm is the most common reason for patients being rejected for EVAR. Short or absent infrarenal neck, large aortic diameters, and excessive angulation at this level are the main problems.

Furthermore, progressive expansion of the aneurysm sac associated with type I endoleak can lead to compromise of seal at the neck and is the principal indication for secondary intervention for this condition.

Means and method for repairing aortic aneurysms, especially an implementable kit and methods thereof useful for treating an aneurysmatic abdominal aorta, avoiding the dislocation of the implanted kit along the aorta, are still a long felt need.

SUMMARY OF THE INVENTION

It is one object of the invention to disclose an implantable kit for treating an aneurysmatic abdominal aorta of a human subject. The kit comprises an endovascular stent-graft (ESG) and an extra-vascular wrapping (EVW). The ESG comprises a structural member (ESG-SM) adjustable between a radially-expanded state and a radially-compressed state; and, a fluid flow guide (FFG) formed of textile strands, substantially impervious to fluids and adjustable between an expanded state and a radially-compressed state; the FFG including a proximal region along which the fluid flow guide is tubular to provide a primary conduit; the FFG being disposed adjacent to the ESG-SM and being securably attached thereto. The EVW has at least one structural member (EVW-SM), e.g., 1, 2, 4, 12, etc., capable of reversibly interchanging between (i) a generally cylindrical expanded state characterized by an inner diameter and a length in the direction of the aorta suitable for surrounding at least an effective portion of the implanted ESG; and (ii) a deformed state suitable for laparoscopic delivery of the EVW from a location outside of the subject's body to a location around the aorta, and vice versa.

It is in the scope of the invention wherein the EVW further comprises at least one medical textile member (e.g., 1, 2, 4, 12, etc.) adapted to at least partially encircle a segment of the aneurysmatic aorta in proximity to the renal arteries, the medical textile member being disposed adjacent to the EVW-SM and being securably attached thereto.

It is further in the scope of the invention wherein the EVW is adapted by means of size and shape to wrap the aorta in a non-continuous manner.

It is also in the scope of the invention wherein the deformed state of the EVW-SM comprises at least one of the following characteristics: (i) longitudinal deformability, adapted to reduce the length in the direction of the aorta and hence allow insertion of the EVW into a laparoscopic channel; and (ii) circular-to-linear deformability, adapted to convert the generally cylindrical to a generally linear configuration, so as to provide the EVW to be pushed through a generally straight laparoscopic channel.

It is another object of the invention to disclose a secured implantable kit for treating an aneurysmatic abdominal aorta of a human subject, comprises at least two attachable elements: an ESG and an EVW. The ESG comprises (i) a structural member (ESG-SM) adjustable between a radially-expanded state and a radially-compressed state; and (ii) a fluid flow guide (FFG) formed of textile strands, substantially impervious to fluids and adjustable between an expanded state and a radially-compressed state; the FFG including a proximal region along which the fluid flow guide is tubular to provide a primary conduit; the FFG being disposed adjacent to the ESG-SM and being securably attached thereto. The EVW has at least one structural member (EVW-SM) e.g., 1, 2, 4, 12, etc., capable of reversibly interchanging between (i) a generally cylindrical expanded state characterized by an inner diameter and a length in the direction of the aorta suitable for surrounding at least an effective portion of the implanted ESG; and (ii) a deformed state suitable for laparoscopic delivery of the EVW from a location outside of the subject's body to a location around the aorta, and vice versa. The EVW-SM and either the ESG-SM or FFG are in attachment therebetween so that dislocation of the implanted kit along the aorta is avoided.

It is in the scope of the invention wherein the attachment comprises a reversible attachment.

It is also in the scope of the invention wherein the EVW additionally comprises a plurality of fastening means, adapted to secure the EVW over the aneurysmatic aorta.

It is also in the scope of the invention wherein the fastening means are selected from a group consisting of threads, screws, hooks, zips, fasteners, clips, flaps, claspers, springs, claspers, staplers, grips, zippers, hooks and corresponding eyes, hook and loop reclosable fastener squares, hook and loop reclosable fastener strips, hook and loop reclosable fastener dots, hooks-and-loops, e.g., Velcro™-type fasteners, straps, holes and string, sutures, wires, cables, tabs, poppers, nails, buttons and corresponding button holes, press buttons brackets, glues, adhesives, or any combination thereof.

It is also in the scope of the invention wherein the attachment is provided by a means of one or more physical members (e.g. utilizing hooks, pins, etc.) connecting directly between the ESG and the EVW.

It is in the scope of the invention wherein the EVW-SM and ESG-SM are adapted by means of size and shape to be interlocked therebetween (e.g., providing the elements as two adjacent pieces of a puzzle).

It is also in the scope of the invention wherein the medical textile member of EVW comprises at least one (e.g., 1, 2, 4, 12, etc.) internal macroporous layer and at least one (e.g., 1, 2, 4, 12, etc.) external microporous layer.

It is also in the scope of the invention wherein the internal macroporous layer is adapted by means of size and shape to be positioned directly over the aneurysmatic abdominal aorta, and comprises voids dimensioned to allow free tissue ingrowth therethrough.

It is also in the scope of the invention wherein the internal macroporous layer is a polymer mesh characterized by a pores ranging in dimension from about 100 µm to about 2 mm.

It is in the scope of the invention wherein the external microporous layer, is made of a smoothly surfaced material, designed to prevent scar tissue formation and attachment thereto and thereby prevent internal organs from sticking thereto.

It is also in the scope of the invention wherein the external microporous layer is adapted by means of size and shape to be sparsely attached to the internal macroporous layer, so as to allow the free tissue ingrowth while preventing scar tissue formation and attachment to the microporous layer.

It is also in the scope of the invention wherein at least one of the internal macroporous layer and external microporous layer comprises attaching means, the means are selected from a group consisting of threads, holes, screws, hooks, zips, fasteners, clips, flaps, claspers, springs, claspers, grips, zippers, hooks-and-loops e.g., Velcro™-type fasteners, sutures, straps, strings, wires, cables, tabs, poppers, nails, buttons, brackets, glue, adhesives, or any combination thereof.

It is also in the scope of the invention wherein the EVW in the expanded state is in the form of a cylinder, the cylinder is adapted for placement adjacently below renal arteries of the aorta.

It is also in the scope of the invention wherein the EVW in the expanded state comprises one or more, complete or partial, interruptions; the cylinder is adapted for placement adjacently above and below renal arteries of the aorta.

It is also in the scope of the invention wherein the interruptions in cylinder are adapted to allow passage of the renal arteries.

It is also in the scope of the invention wherein the interruptions in cylinder are adapted to allow passage of an inferior mesenteric artery exiting from the aorta.

It is also in the scope of the invention wherein the interruptions in cylinder are adapted to allow passage of a celiac artery exiting from the aorta.

It is also in the scope of the invention wherein the EVW-SM is made of a super-elastic metal.

It is also in the scope of the invention wherein the super-elastic metal is Nitinol.

It is also in the scope of the invention wherein length of EVW in the expanded state is in the range between about 1 to 3 centimeters.

It is also in the scope of the invention wherein the inner diameter of EVW in the expanded state is in the range between about 2 to 4 centimeters.

Another object of the present invention is to disclose an extra-vascular ring (EVR) adapted to at least partially encircle a segment of an aneurysmatic aorta of a human subject in proximity to the renal arteries. The EVR comprises a generally cylindrical inner surface, an outer surface and a structural member; the inner surface and the outer surface are attached therebetween. The fastening means adapted to secure the EVR over the aneurysmatic aorta; EVR is capable of having an expanded state and a deformed state. The EVR in the expanded state is adapted for extra-vascular positioning around the aorta and the EVR in its deformed state is adapted for laparoscopic delivery from a location outside the subject's body to a location around the aorta; the inner surface defining a lumen that is characterized by a proximal circumference, a distal circumference and a length in the proximal to distal direction; the outer surface is characterized by a proximal circumference, a distal circumference and a length in the proximal to distal direction; the inner surface comprises a macroporous medical textile member, comprises voids dimensioned to allow free tissue ingrowth therethrough, and the outer surface comprises a microporous medical textile member that is made of a smoothly surfaced material, designed to inhibit scar tissue formation and attachment thereto and thereby prevent internal organs from sticking thereto. The structural member is connected either to the inner surface or to the outer surface.

It is also in the scope of the invention wherein the EVR further comprises a plurality of fastening means, e.g., 1, 2, 4, 12, 50, etc.

It is also in the scope of the invention wherein the EVR further comprises a plurality of radially projecting attachment means (e.g., 1, 2, 4, 12, etc.). The attachment means being adapted to secure the EVR either to the aorta or to an endovascular aortic stent-graft.

It is also in the scope of the invention wherein the inner surface and the outer surface are substantially concentrically aligned.

It is also in the scope of the invention wherein the inner surface and the outer surface are radially spaced by a distance in the range between about 2 to 5 millimeters.

It is also in the scope of the invention wherein the proximal circumference of outer surface substantially coincides with the proximal circumference of inner surface.

It is also in the scope of the invention wherein the distal circumference of outer surface substantially coincides with the distal circumference of inner surface.

It is also in the scope of the invention wherein the outer surface is substantially tubular.

It is also in the scope of the invention wherein the structural member is made of a superelastic metal.

It is also in the scope of the invention wherein the inner surface and the outer surface are attached thereto via a plurality of spacing members, the spacing members being connected to the structural member.

It is also in the scope of the invention wherein the spacing members are substantially oriented in the radial direction.

It is another object of the present invention to disclose a method for treating an aneurysmatic aorta. The method comprises steps selected from the following: (a) identifying a subject having a medical condition indicative of an unacceptably high risk of rupture of an aneurysm of the abdominal aorta; (b) providing an implantable kit as defined in any of the above; (c) introducing the EVW in the deformed state through a laparoscopic working channel to an abdominal location adjacent to renal arteries of the abdominal aorta; (d) laparoscopically positioning the EVW around the aorta, in vicinity to renal arteries; and (e) endovascularly placing the endovascular stent-graft (ESG) into the aneurysmatic aorta in the subject.

It is also in the scope of the invention wherein the ESG and the EVW are attachable therebetween and wherein method further comprises step (f); step (f) comprises attaching the EVW and the ESG therebetween in a manner that a dislocation of the implanted kit along the aorta is avoided.

It is also in the scope of the invention wherein the attachable comprises reversibly attachable and wherein the attaching comprises reversibly attaching.

It is also in the scope of the invention wherein the step of identifying a subject having a medical condition indicative of an unacceptably high risk of rupture of an aneurysm of the abdominal aorta comprises identifying a subject having a medical condition indicative of an unacceptably high risk of rupture of an aneurysm of the abdominal aorta and the aneurysm reaching about 2 centimeters or less to a closest renal artery of the subject.

It is also in the scope of the invention wherein the aforesaid method further comprises the steps of (a) upon identification of Type I endoleak—introducing the EVW in a deformed state through a laparoscopic working channel to an abdominal location adjacent to renal arteries of the abdominal aorta of the subject and laparoscopically positioning the EVW around the aorta, in vicinity to renal arteries.

It is another object of the invention to disclose a method for treating an aneurysmatic aorta. The method comprises steps selected from the following: (a) identifying a subject having a medical condition indicative of an unacceptably high risk of rupture of an aneurysm of the abdominal aorta; (b) providing a fastened implantable kit for treating an aneurysmatic abdominal aorta, comprises at least the elements of ESG, EVW, and plurality (e.g., 1, 2, 4, 12, 50, etc.) of fastening means, adapted to secure the EVW over the aneurysmatic aorta; (c) introducing the EVW in the deformed state through a laparoscopic working channel to an abdominal location adjacent to renal arteries of the abdominal aorta of the subject; (d) laparoscopically positioning the EVW around the aorta, in vicinity to renal arteries; (e) connecting the corresponding fastening means therebetween; and (f) endovascularly placing the ESG into the aneurysmatic aorta.

It is also in the scope of the invention wherein the step of identifying a subject having a medical condition indicative of an unacceptably high risk of rupture of an aneurysm of the abdominal aorta comprises identifying a subject having a medical condition indicative of an unacceptably high risk of rupture of an aneurysm of the abdominal aorta and the aneurysm reaching about 2 centimeters or less to a closest renal artery of the subject.

It is also in the scope of the invention wherein the method further comprises the steps of (a) upon identification of Type I endoleak—introducing the EVW in a deformed state through a laparoscopic working channel to an abdominal location adjacent to renal arteries of the abdominal aorta of the subject and laparoscopically positioning the EVW around the aorta, in vicinity to renal arteries and connecting the corresponding fastening means to one another.

BRIEF DESCRIPTION OF THE FIGURES

The present invention will now be described, by way of example only, with respect to the accompanying figures, wherein.

DETAILED DESCRIPTION OF THE EMBODIMENTS

Figure 1A:
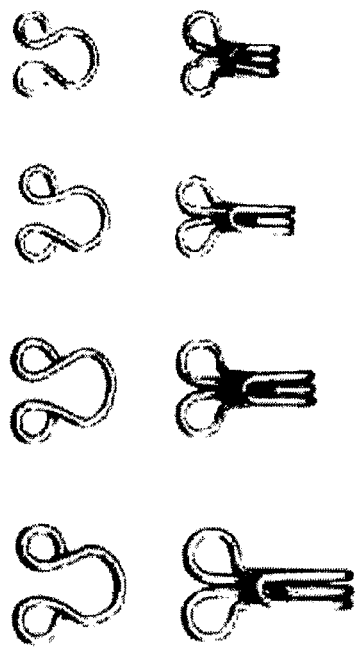
FIGS. 1A to 1D depict different variants of fasteners according to few embodiments of the invention.
Figure 1B:
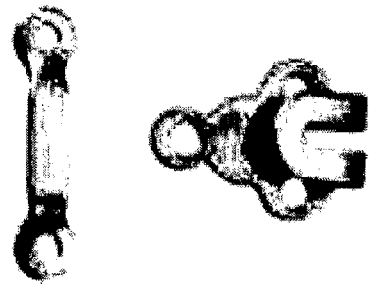
Figure 1C:
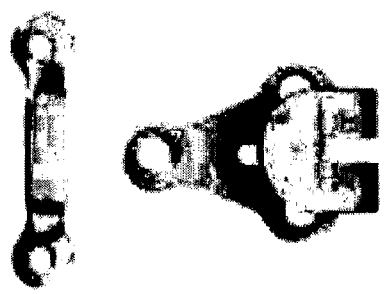
Figure 1D:

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide an implementable kit and EVR for treating an aneurysmatic abdominal aorta and methods thereof.

It is one embodiment of the invention wherein an implementable kit for treating an aneurysmatic abdominal aorta is disclosed. The kit comprises at least two attachable elements: an endovascular stent-graft (ESG) and an extra-vascular wrapping (EVW). The ESG comprises a structural member (ESG-SM) adjustable between an expanded state and a radially-deformed state; and a fluid flow guide (FFG) formed of textile strands, substantially impervious to fluids and adjustable between an expanded state and a radially-deformed state; the FFG including a proximal region along which the fluid flow guide is tubular to provide a primary conduit. The EVW comprises an extra-vascular wrapping (EVW), the EVW having at least one (e.g., 1, 2, 4, 12, etc.) structural member (EVW-SM), capable of reversibly interchanging between (i) an expanded state characterized by an inner diameter and a length in the direction of the aorta suitable for surrounding at least an effective portion of the implanted ESG; and (ii) a deformed state suitable for laparoscopic delivery to a location around the aorta, and vice versa. The EVW-SM and either the ESG-SM or FFG are at least reversibly attachable in a manner that a dislocation of the implanted kit along the aorta is avoided.

It is another embodiment of the invention wherein a secured kit is disclosed. Here, the aforesaid EVW additionally comprises a plurality (e.g., 1, 2, 4, 12, 50, etc.) of fastening means, adapted to secure the EVW over the aneurysmatic aorta. The fastening means are selected in a non-limiting manner from a group consisting of threads, screws, hooks, zips, fasteners, clips, flaps, claspers, springs, claspers, staplers, grips, zippers, hooks and corresponding eyes, hook and loop reclosable fastener squares, hook and loop reclosable fastener strips, hook and loop reclosable fastener dots, hooks-and-loops, e.g., Velcro™-type fasteners, straps, holes and string, wires, cables, tabs, poppers, nails, buttons and corresponding button holes, press buttons brackets, glues, adhesives, or any combination thereof.

It is well in the scope of the invention, wherein the term 'secured' refers interchangeably to at least two different relevant meanings, namely:

(a) securing of the EVW to the aorta; and
(b) securing (or otherwise attaching) of the EVW to the ESG.

It is well in the scope of the invention, wherein the term 'endoleak' refers to Type I Endoleak, which comprises a failure to seal attachment sites of an endovascular stent-graft to the native vessels. This is widely recognized as the type of endoleak that is most closely linked to rupture and is therefore the most aggressively treated.

Another embodiment of the invention wherein an extra-vascular ring (EVR) is disclosed. The EVR is adapted to at least partially encircle a segment of an aneurysmatic aorta in proximity to the renal arteries. The EVR comprises a substantially tubular inner surface, an outer surface and a plurality of fastening means; the inner surface and the outer surface are attached thereto; the fastening means adapted to secure the EVR over the aneurysmatic aorta. The EVR is capable of having an expanded state and a deformed state. The EVR in the expanded state is adapted for extra-vascular positioning around an aorta and the EVR in the deformed state is adapted for laparoscopic delivery to a location around the aorta. The inner surface defining a lumen that is characterized by a proximal circumference, a distal circumference and a length in the proximal to distal direction; the outer surface is characterized by a proximal circumference, a distal circumference and a length in the proximal to distal direction. The inner surface may comprises (i) a macroporous medical textile member, comprises voids dimensioned to allow free tissue ingrowth therethrough, and (ii) a structural member connected thereto. The outer surface may comprises (i) a microporous medical textile member that is made of a smoothly surfaced material, designed to prevent scar tissue formation and attachment thereto and thereby prevent internal organs from sticking thereto and (ii) a structural member disposed therein and attached thereto.

Still another embodiment of the invention wherein method for treating an aneurysmatic aorta. The method comprises steps selected from the following: (a) identifying a subject having a medical condition indicative of an unacceptably high risk of rupture of an aneurysm of the abdominal aorta; (b) obtaining an implementable kit as defined in any of the above; (c) introducing the EVW in a deformed state through a laparoscopic working channel to an abdominal location adjacent to renal arteries of the abdominal aorta of the subject; (d) laparoscopically positioning the EVW around the aorta, in vicinity to renal arteries; (e) introducing a healing period of no less than 1 week; (f) endovascularly placing the Endovascular stent-graft (ESG) into the aneurysmatic aorta in the subject; and (g) at least reversibly detaching the EVW-SM and either the ESG-SM or FFG in a manner that a dislocation of the implanted kit along the aorta is avoided.

A further embodiment of the invention wherein another method for treating an aneurysmatic aorta is disclosed. The method comprises steps selected from the following: (a) identifying a subject having a medical condition indicative of an unacceptably high risk of rupture of an aneurysm of the abdominal aorta; (b) obtaining a fastened implementable kit for treating an aneurysmatic abdominal aorta, as defined above, namely a kit comprises a plurality of fastening means, adapted to secure the EVW over the aneurysmatic aorta; (c) introducing the EVW in a deformed state through a laparoscopic working channel to an abdominal location adjacent to renal arteries of the abdominal aorta of the subject; (d) laparoscopically positioning the EVW around the aorta, in vicinity to renal arteries; (e) connecting the corresponding fastening means to one another; (f) introducing a healing period of no less than 1 week; (g) endovascularly placing the ESG into the aneurysmatic aorta in the subject; and (h) securing the kit by fastening the fastening means and hence at least reversibly detaching the EVW-SM and either the ESG-SM or FFG in a manner that a dislocation of the implanted kit along the aorta is avoided Reference is now made to the figures schematically presenting in a non-limiting manner out-of-scale presentations of various embodiments of the invention. FIGS. 1A to 1D depict different variants of fasteners: hooks and loops reclosable fastener stripes (e.g. hooks) and hatched stripes denote the complementary (e.g. loops) type of hooks and loops reclosable fastener stripes.

Figure 2:
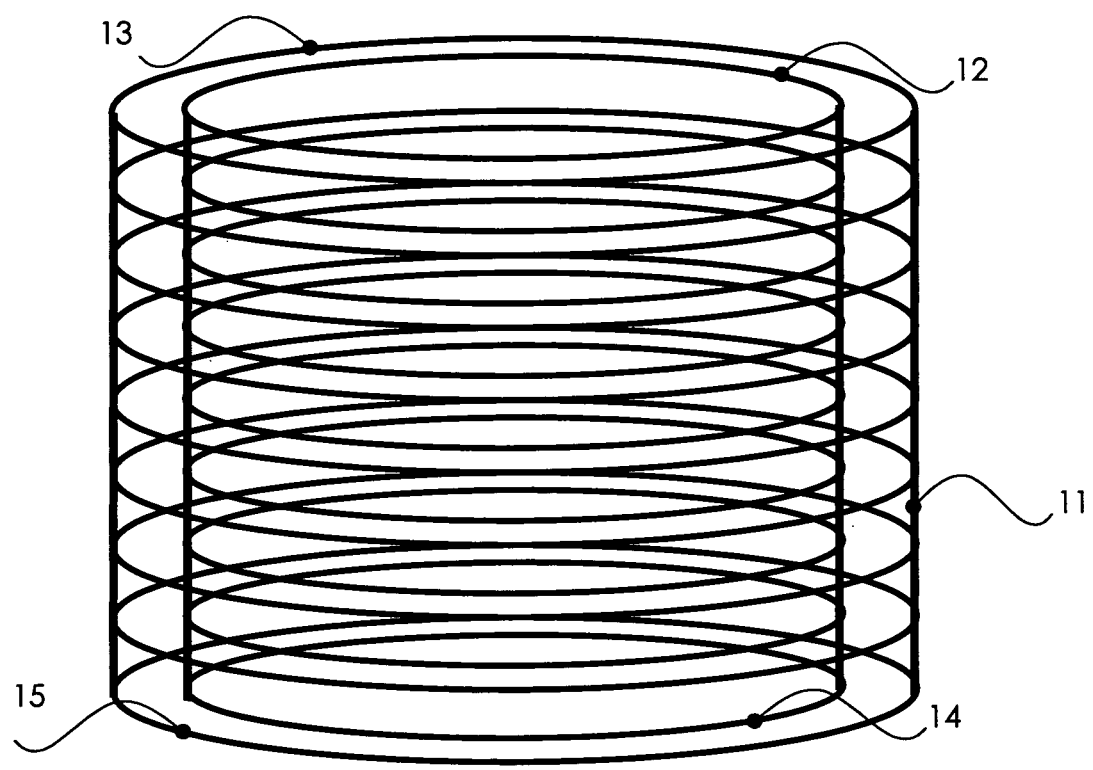
FIG. 2 depicts an EVR according to another embodiment of the invention.

FIG. 2 depicts an Extra Vascular Ring wherein the inner surface (10) and the outer surface (11) are concentrically aligned and are radially spaced by a substantially constant distance.

Figure 3:
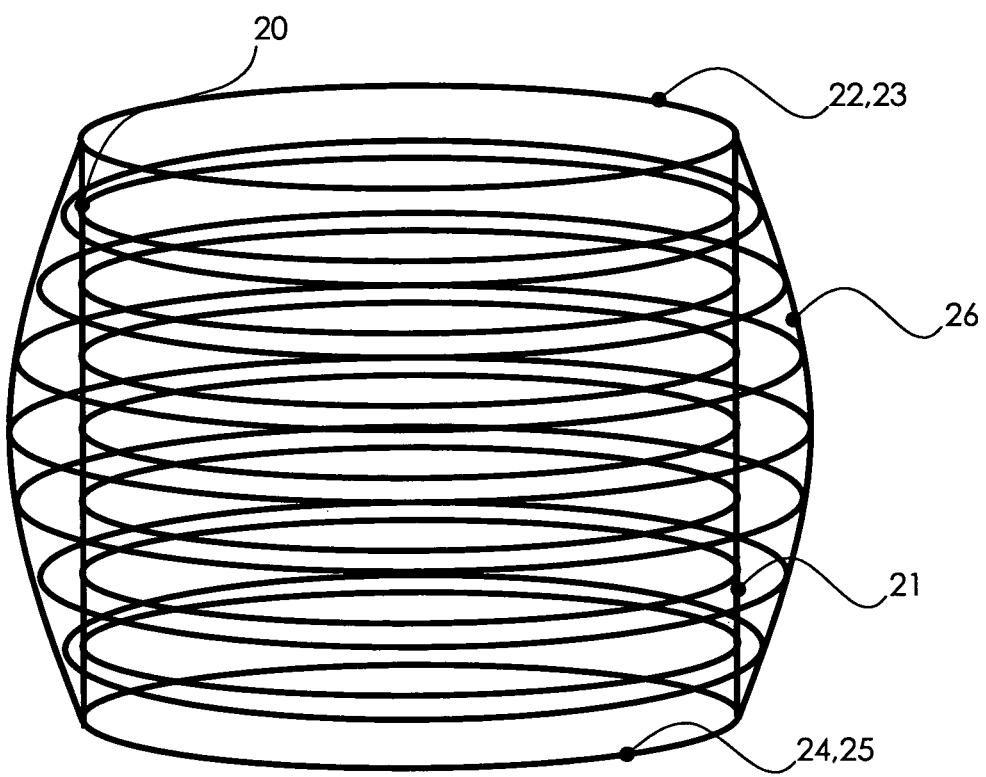
FIG. 3 depicts an EVR according to yet another embodiment of the invention.

FIG. 3 depicts an Extra Vascular Ring comprising an inner surface (20) and an outer surface (16) wherein the distal circumference of outer surface (25) substantially coincides with the distal circumference of inner surface (24) and wherein the proximal circumference of outer surface (23) substantially coincides with the proximal circumference of its inner surface (22).

Figure 4:
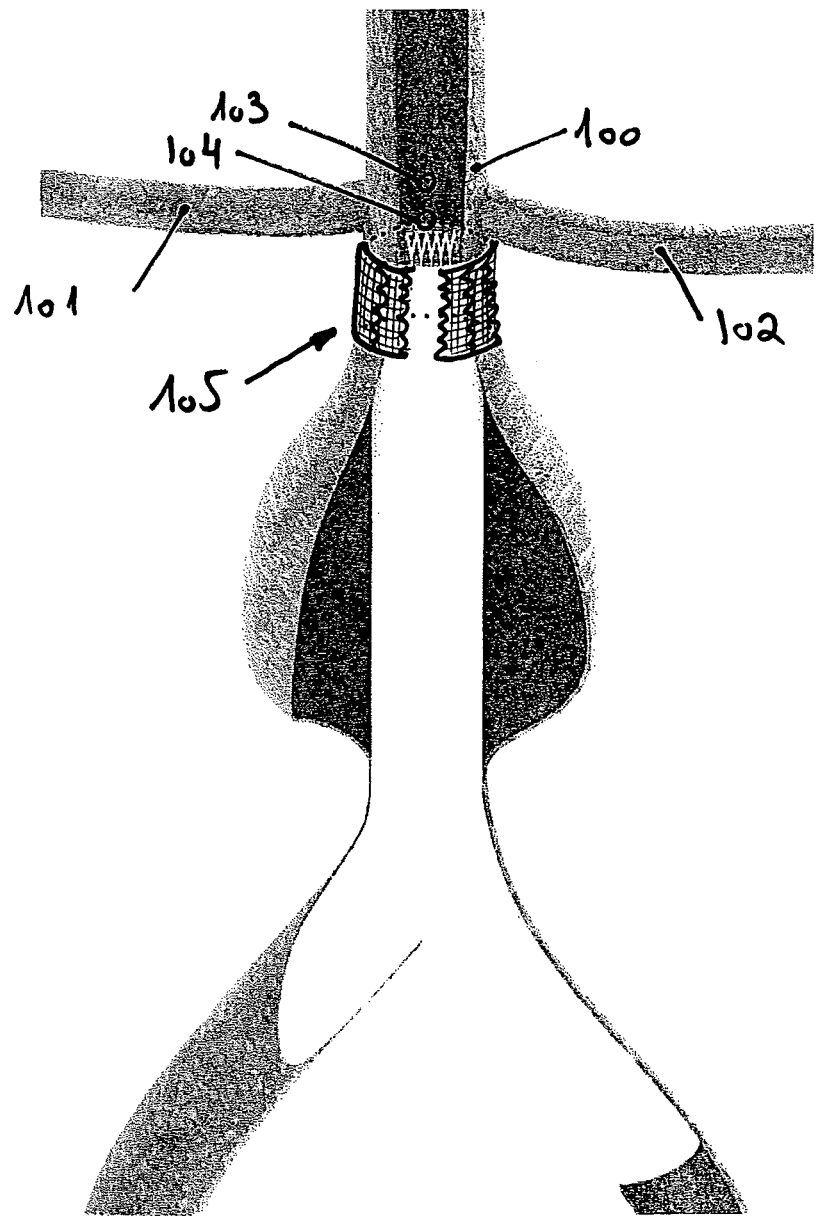
FIG. 4 depicts an EVR according to yet another embodiment of the invention.

FIG. 4 depicts an abdominal aorta (100), a right renal artery (101), a left renal artery (102), a celiac artery (103) and an inferior mesenteric artery (104). An extra-vascular wrapping (105) is positioned adjacently below the renal arteries.

Figure 5:
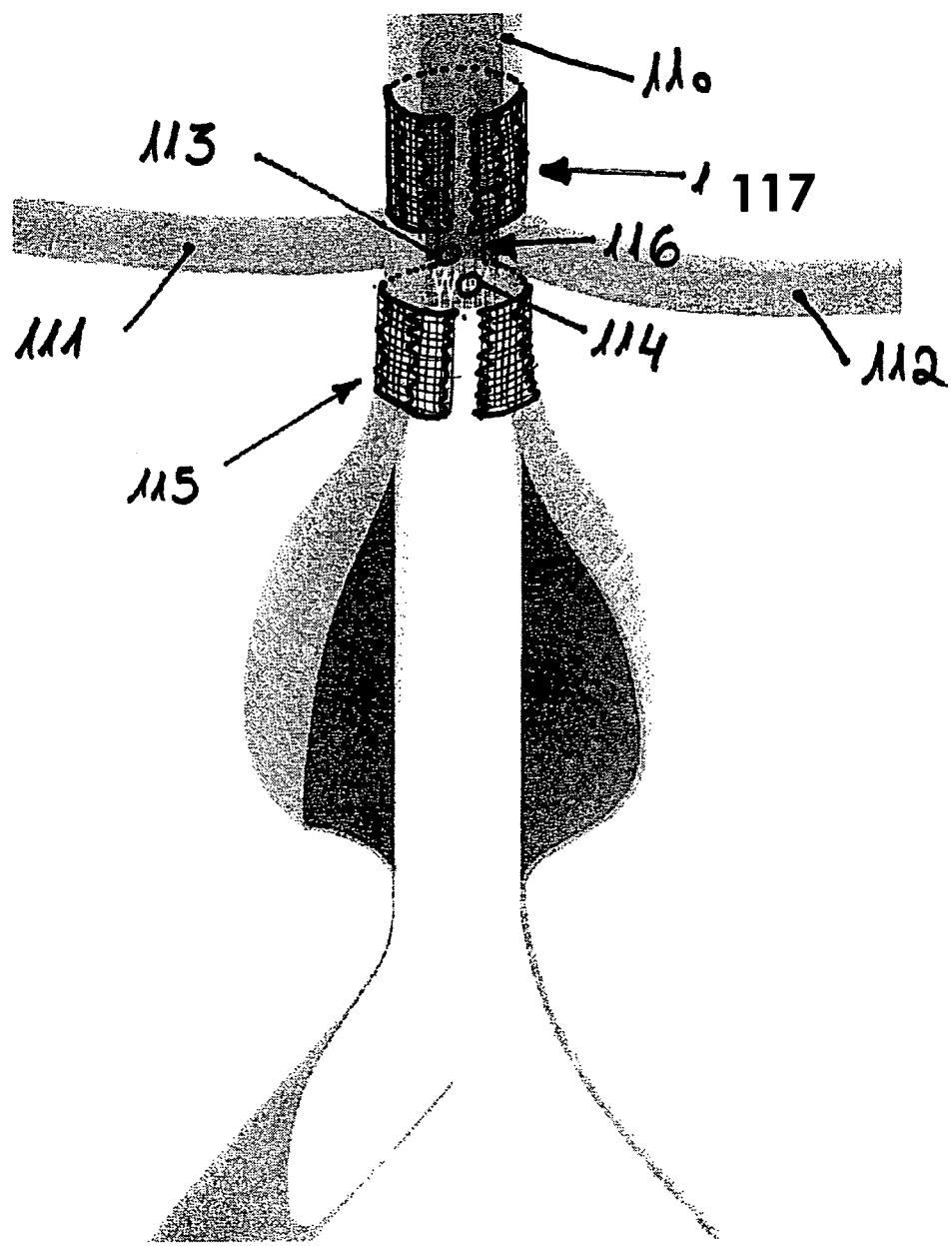
FIG. 5 depicts an EVR according to yet another embodiment of the invention.

FIG. 5 depicts an abdominal aorta (110), a right renal artery (111), a left renal artery (112), a celiac artery (113) and an inferior mesenteric artery (114). Further depicted is an extra-vascular wrapping having a distal section (115) that is positioned adjacently below the renal arteries (111, 112) and a proximal section (117) that is positioned adjacently below the renal arteries (111, 112) and a bridging section (116) that connects between the distal section (115) and the proximal section (117).

Figure 6:
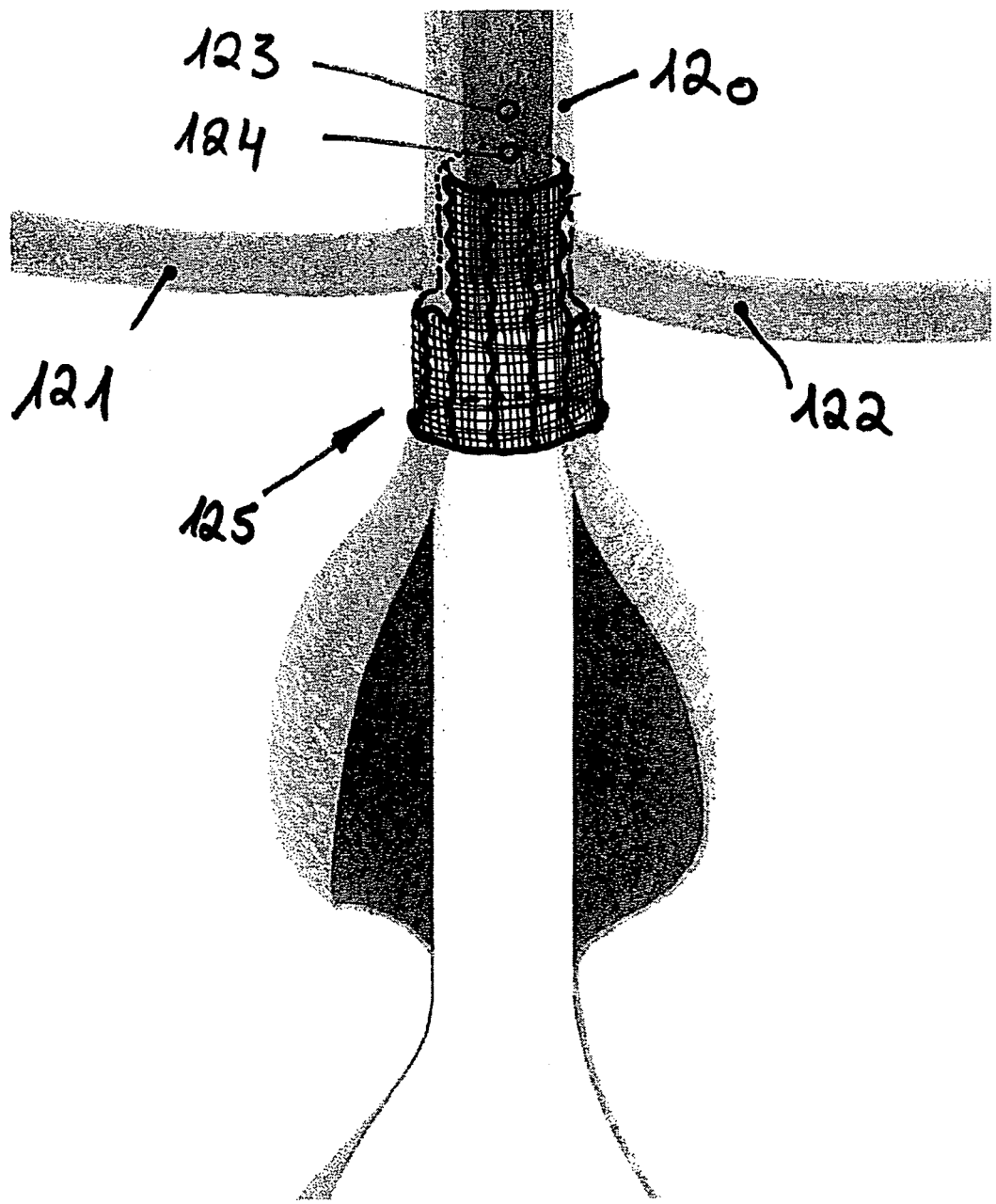
FIG. 6 depicts an EVR according to yet another embodiment of the invention.

FIG. 6 depicts an abdominal aorta (120), a right renal artery (121), a left renal artery (122), a celiac artery (123) and an inferior mesenteric artery (124). An extra-vascular wrapping (125) is positioned adjacently below the renal arteries and is adapted to allow renal arteries (121, 122) to exit through a substantially side-looking recesses in extra-vascular wrapping (125).

Figure 7:
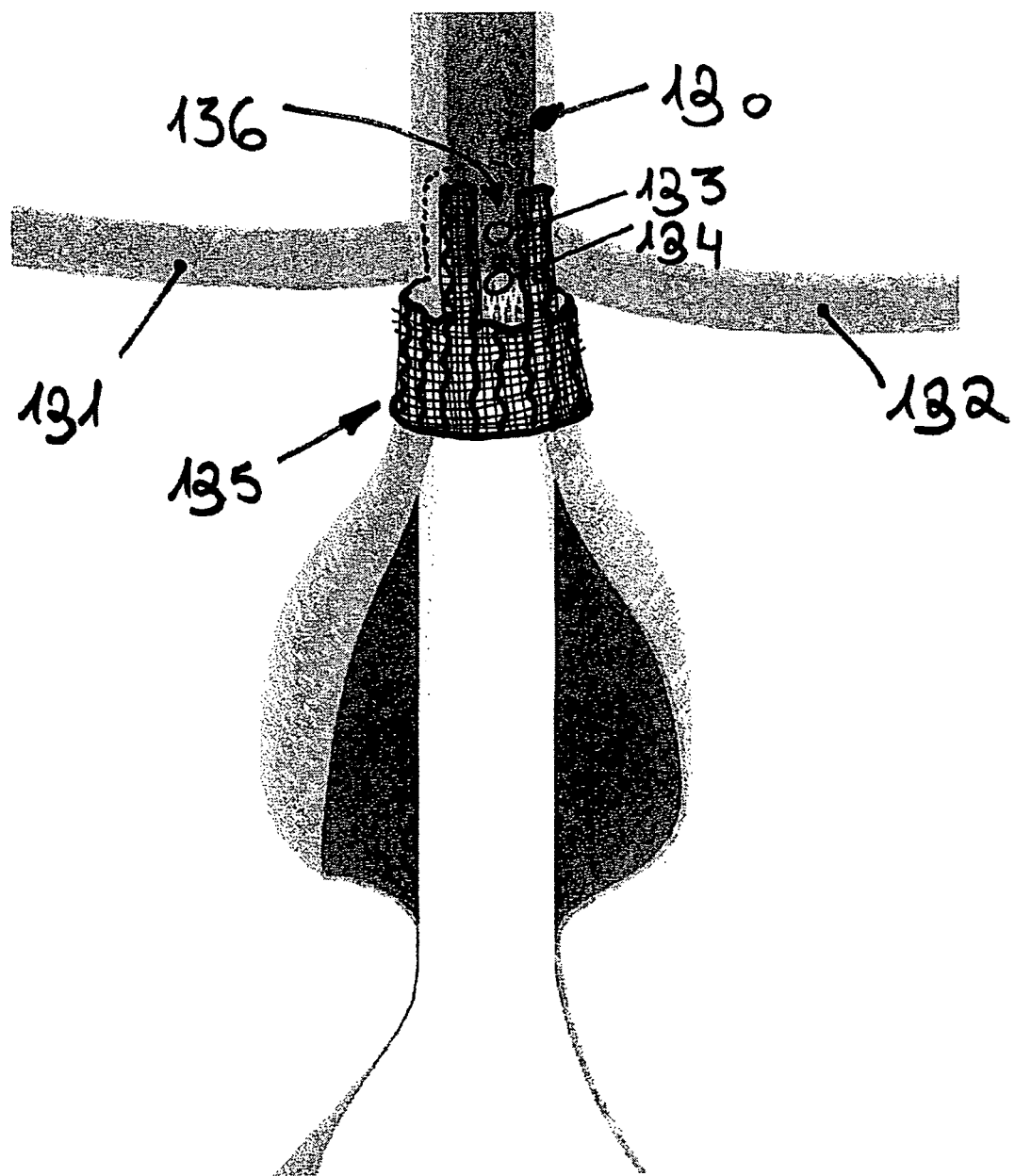
FIG. 7 depicts an EVR according to yet another embodiment of the invention.

FIG. 7 depicts an abdominal aorta (130), a right renal artery (131), a left renal artery (132), a celiac artery (133) and an inferior mesenteric artery (134). An extra-vascular wrapping (135) is positioned adjacently below the renal arteries (131; 132) and is adapted to allow renal arteries (131, 132) to exit through a substantially side-looking recesses in extra-vascular wrapping (135). The extra-vascular wrapping (135) further allows the celiac artery (133) and the inferior mesenteric artery (134) to exit through a substantially forward-looking recess.

Figure 8A:
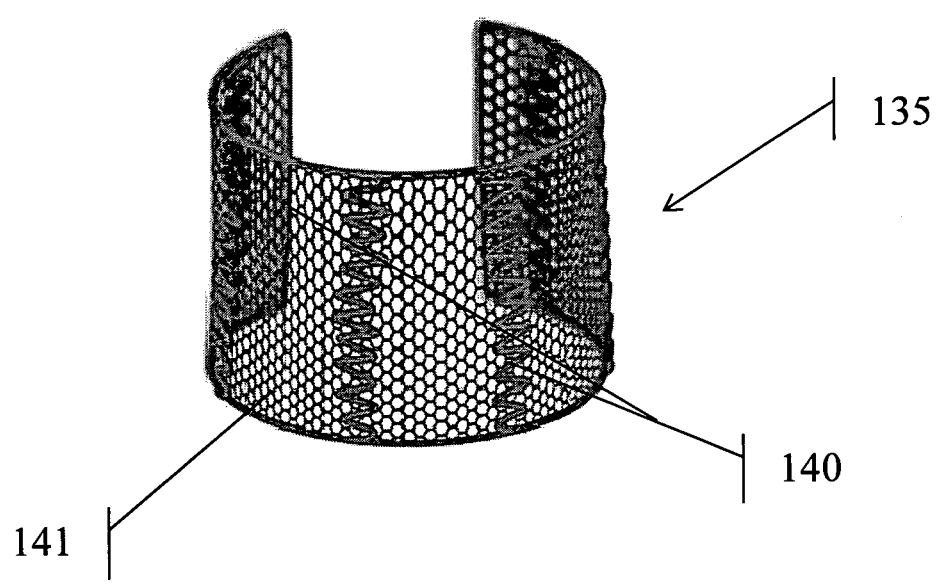
FIG. 8A depicts an extra-vascular wrapping (135), which include a structural member (140) and a medical textile member (141)

FIG. 8A depicts an extra-vascular wrapping (135), which include a structural member (140) and a medical textile member (141).

Figure 8B:
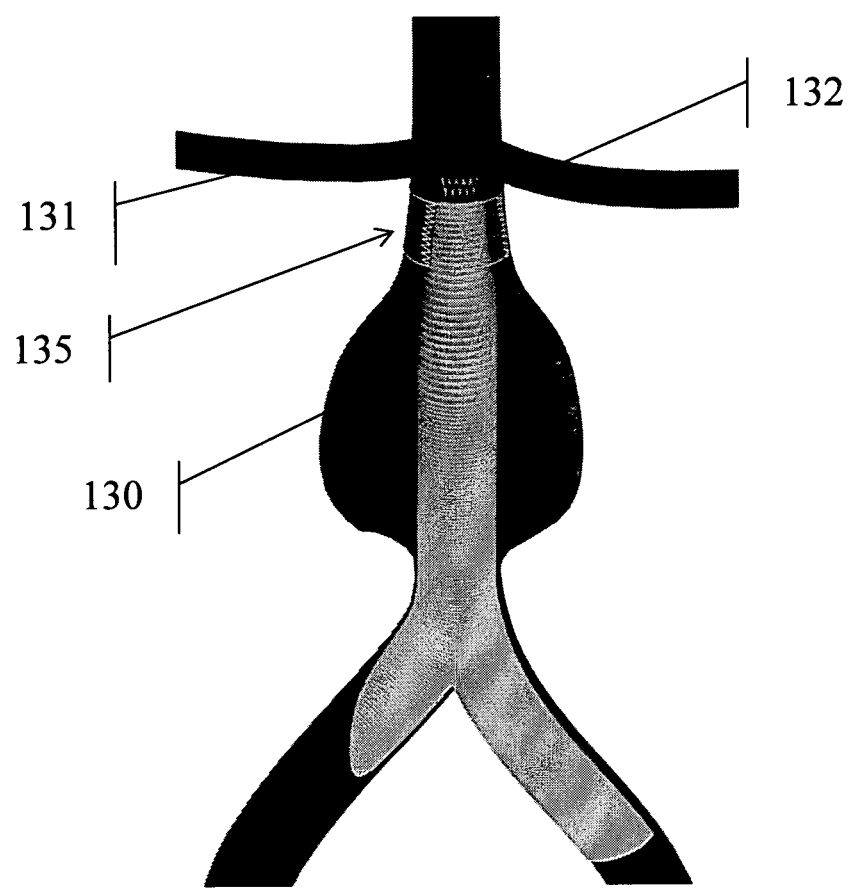
FIG. 8B depicts an abdominal aorta (130), a right renal artery (131), a left renal artery (132), over which the extra-vascular wrapping (135) of FIG. 8a is positioned, adjacently below the renal arteries (131, 132) and is adapted to allow renal arteries (131, 132) to exit thereabove.

FIG. 8B depicts an abdominal aorta (130), a right renal artery (131), a left renal artery (132), over which the extra-vascular wrapping (135) of FIG. 8a is positioned, adjacently below the renal arteries (131, 132) and is adapted to allow renal arteries (131, 132) to exit thereabove.

Figure 9A:
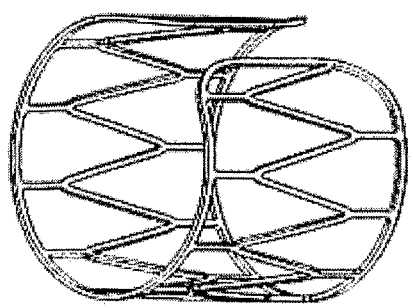
FIG. 9A depicts an isometric view of the structural member of the extra vascular wrapping.

FIG. 9A depicts an isometric view of the structural member of the extra vascular wrapping.

Figure 9B:
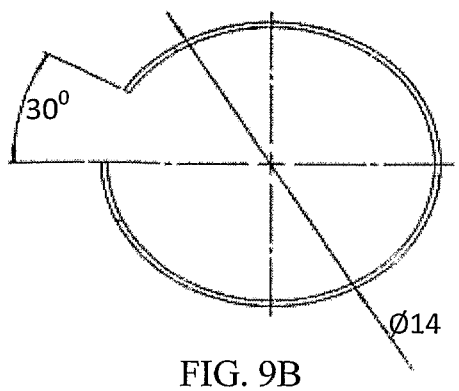
FIG. 9B depicts an axial view of the structural member of the extra vascular wrapping.

FIG. 9B depicts an axial view of the structural member of the extra vascular wrapping.

Figure 9C:
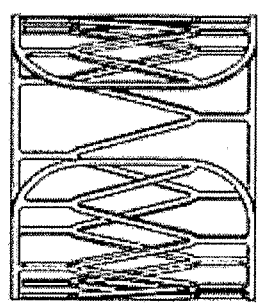
FIG. 9C depicts a side view of the structural member of the extra vascular wrapping.

FIG. 9c depicts a side view of the structural member of the extra vascular wrapping.

Figure 9D:
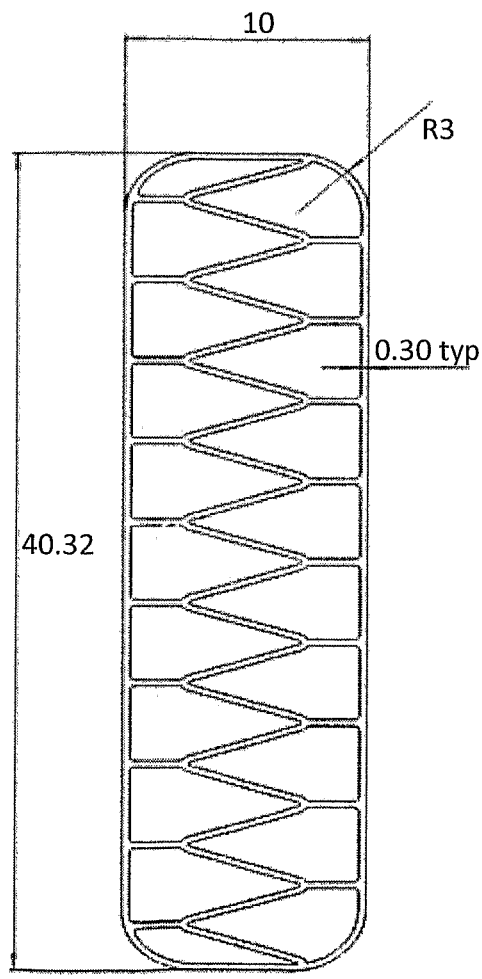
FIG. 9D depicts a view of a circularly-to-linearly deformed structural member of the extra vascular wrapping.

FIG. 9D depicts a view of a circularly-to-linearly deformed structural member of the extra vascular wrapping.

Figure 9E:
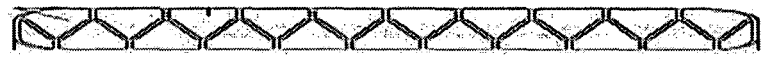
FIG. 9E depicts a view of a circularly-to-linearly deformed and a longitudinally deformed structural member of the extra vascular wrapping.

FIG. 9E depicts a view of a circularly-to-linearly deformed and a longitudinally deformed structural member of the extra vascular wrapping, so that it facilitates insertion of the extra vascular wrapping into a laparoscopic channel.

The invention claimed is:

1. An implantable kit for treating an aneurysmatic abdominal aorta of a human subject, the kit comprising:
   an endovascular stent-graft (ESG) comprising:
   a structural member (ESG-SM) adjustable between a radially-expanded state and a radially-compressed state; and
   a fluid flow guide (FFG), substantially impervious to fluids and adjustable between an expanded state and a radially-compressed state; said FFG including a proximal region along which the fluid flow guide is tubular to provide a primary conduit; and said FFG being disposed adjacent to said ESG-SM and being securely attached thereto; and
   an extra-vascular wrapping (EVW) comprising:
   at least one structural member (EVW-SM), capable of reversibly interchanging between (i) a generally cylindrical expanded state characterized by an inner diameter and a length in the direction of said aorta suitable for surrounding at least an effective portion of said ESG; and (ii) a deformed state suitable for laparoscopic delivery of said EVW from a location outside of said subject's body to a location around said aorta, and vice versa; and
   at least one medical textile member adapted to at least partially encircle a segment of said aneurysmatic aorta in proximity to the renal arteries, said medical textile member (a) being disposed adjacent to said EVW-SM and being securely attached thereto, and (b) comprising at least one internal macroporous layer, which comprises a polymer mesh characterized by pores ranging in dimension from 100 µm to 2 mm, the macroporous layer being adapted by means of size and shape to be positioned directly over said aneurysmatic abdominal aorta, and shaped so as to define voids dimensioned to allow free tissue ingrowth therethrough, wherein said EVW-SM and either said ESG-SM or said FFG are in reversible attachment therebetween by one or more physical members connecting directly between said ESG and said EVW, so that dislocation of the kit along the aorta is avoided.

2. The kit according to claim 1, wherein said medical textile member comprises at least one external microporous layer.

3. The kit according to claim 2, wherein said external microporous layer comprises a smoothly surfaced material, configured to prevent scar tissue formation and attachment thereto and thereby prevent internal organs from sticking thereto, and wherein said external microporous layer is adapted by means of size and shape to be sparsely attached to said internal macroporous layer, so as to allow said free tissue ingrowth while preventing scar tissue formation and attachment to said microporous layer.

4. The kit according to claim 2, wherein at least one of said internal macroporous layer and said external microporous layer comprises attaching elements selected from the group consisting of: threads, holes, screws, hooks, zips, fasteners, clips, flaps, claspers, springs, grips, zippers, hooks-and-loops, sutures, straps, strings, wires, cables, tabs, poppers, nails, buttons, brackets, glue, adhesives, and any combination thereof.

5. The kit according to claim 1, wherein said EVW is adapted by means of size and shape to wrap said aorta in a non-continuous manner.

6. The kit according to claim 1, wherein said deformed state of said EVW-SM comprises at least one of the following characteristics: a. longitudinal deformability, adapted to reduce said length in the direction of said aorta and hence allow insertion of said EVW into a laparoscopic channel; and b, circular-to-linear deformability, adapted to convert said generally cylindrical to a generally linear configuration, so as to provide the EVW to be pushed through a generally straight laparoscopic channel.

7. The kit according to claim 1, wherein said EVW additionally comprises a plurality of fastening elements, adapted to secure said EVW over said aneurysmatic aorta, which fastening elements are selected from the group consisting of: threads, screws, hooks, zips, fasteners, clips, flaps, claspers, springs, staplers, grips, zippers, hooks and corresponding eyes, hook and loop reclosable fastener squares, hook and loop reclosable fastener strips, hook and loop reclosable fastener dots, hooks-and-loops, straps, holes and string, sutures, wires, cables, tabs, poppers, nails, buttons and corresponding button holes, press buttons brackets, glues, adhesives, and any combination thereof.

8. The kit according to claim 1, wherein said EVW-SM and ESG-SM are adapted by means of size and shape to be interlocked therebetween.

9. The kit according to claim 1, wherein said EVW when in said expanded state is in the form of a cylinder, wherein said cylinder is adapted for placement adjacently below renal arteries of said aorta, wherein said EVW when in said expanded state comprises one or more complete or partial interruptions, and wherein said cylinder is adapted for placement adjacently above and below said renal arteries of said aorta.

10. The kit according to claim 9, wherein said cylinder comprises interruptions adapted to allow passage of at least one artery selected from the group consisting of: (a) said renal arteries; (b) an inferior mesenteric artery exiting from said aorta; (c) a celiac artery exiting from said aorta; and (d) any combination thereof.

11. The kit according to claim 1, wherein said EVW-SM comprises a super-elastic metal selected from Nitinol or any alloy thereof.

12. The kit according to claim 1, wherein said length of said EVW-SM when in said expanded state is in the range between 1 to 3 centimeters, and wherein said inner diameter of said EVW-SM in its said expanded state is in the range between 2 to 4 centimeters.

13. A method for treating an aneurysmatic aorta, comprising:
identifying a subject suffering from an aneurysm of the abdominal aorta;
providing a fastenable implantable kit for treating said aneurysmatic abdominal aorta, comprising at least (i) an endovascular stent-graft (ESG) comprising: (a) a structural member (ESG-SM) adjustable between an expanded state and a radially-compressed state; and (b) a fluid flow guide (FFG), substantially impervious to fluids and adjustable between an expanded state and a radially-compressed state; said FFG including a proximal region along which the fluid flow guide is tubular to provide a primary conduit; and (ii) an extra-vascular wrapping (EVW), said EVW having at least one structural member (EVW-SM), capable of reversibly interchanging between (x) a generally cylindrical expanded state characterized by an inner diameter and a length in the direction of said aorta suitable for surrounding at least an effective portion of said implanted ESG; and (y) a deformed state suitable for laparoscopic delivery of said EVW from a location outside of said subject's body to a location around said aorta, and vice versa; and
introducing said EVW in said deformed state through a laparoscopic working channel to an abdominal location adjacent to renal arteries of said abdominal aorta of said subject;
laparoscopically positioning said EVW around said aorta, in a vicinity of said renal arteries;
endovascularly placing the ESG into said aneurysmatic aorta; and
connecting directly between said ESG in said aneurysmatic aorta and said EVW around said aorta, using one or more physical members.

14. The method according to claim 13, wherein identifying such subject as suffering from such aneurysm of the abdominal aorta comprises identifying a subject suffering from an aneurysm of the abdominal aorta, which aneurysm reaches about 2 centimeters or less to a closest renal artery of said subject.

* * * * *